United States Patent [19]

Boutonnat et al.

[11] Patent Number: 4,538,448
[45] Date of Patent: Sep. 3, 1985

[54] METHOD AND DEVICE FOR DETERMINING OF EXPLOSIVITY RATE OF GASEOUS MEDIUM

[75] Inventors: Maurice Boutonnat, Gouvieux; Christian Marget, Verneuil-en-Halatte, both of France

[73] Assignee: Charbonnages de France, Paris, France

[21] Appl. No.: 558,734

[22] Filed: Dec. 6, 1983

[30] Foreign Application Priority Data

Dec. 14, 1982 [FR] France ................................ 82 20925

[51] Int. Cl.$^3$ ............................................. G01N 25/54
[52] U.S. Cl. ...................................... 73/27 R; 422/94
[58] Field of Search ................... 73/23, 27 R; 340/632, 340/633, 634; 422/94, 95, 96, 98; 364/577, 497

[56] References Cited

U.S. PATENT DOCUMENTS

| | | | |
|---|---|---|---|
| 3,449,939 | 6/1969 | Monomakhoff | 73/27 R |
| 3,587,318 | 6/1971 | Belugou et al. | 73/204 |
| 4,140,004 | 2/1979 | Smith et al. | 73/26 |
| 4,388,822 | 6/1983 | Heller | 340/632 |
| 4,422,073 | 12/1982 | Winner | 340/632 |
| 4,475,378 | 10/1984 | Boutonnat et al. | 73/23 |

FOREIGN PATENT DOCUMENTS 2117514 7/1972 France .

Primary Examiner—Stephen A. Kreitman
Attorney, Agent, or Firm—Karl W. Flocks; Sheridan Neimark; A. Fred Starobin

[57] ABSTRACT

A method and a device for determining explosivity rate of a gaseous medium with a detecting filament which is heated in said medium by an electric current flowing therethrough. Said detecting filament is ignited through connection to a power supply and power supplied to said filament is regulated so as to maintain constant the resistance thereof. At some successive moments value of a quantity U significant for power supplied to said filament is taken into account. An exponential curve is extrapolated from such values; parameters thereof are identified and introduced in a process function adapted to deduce therefrom an estimation of the initial explosivity rate of said gaseous medium independently of the nature of the explosive gas(es) present therein.

23 Claims, 12 Drawing Figures

METHOD AND DEVICE FOR DETERMINING OF EXPLOSIVITY RATE OF GASEOUS MEDIUM

BACKGROUND OF THE INVENTION

This invention relates generally to the detection of explosive gases in a gaseous medium such as air.

In a manner known in itself, the the detection of explosive gas in air is performed in an apparatus usually called catalytic filament explosimeter in which a filament generally of platinum is heated by Joule effect i.e. by the passage of an electric current therein. The explosive gas contained in air oxidizes by catalysis upon contacting the filament, thereby causing additional heating of the latter. The increase in temperature resulting therefrom causes increased resistance of the filament and measurement of such resistance gives access to the concentration of such explosive gas in air. Practically, it is dealt with the gas explosivity level i.e. the ratio of its concentration to its lower limit of explosiveness (LIE), i.e. the gas content above which there is a risk of explosion; this is why the detection result is usually presented as a percentage of the mentioned limit LIE.

By way of example the Applicant has proposed in its U.S. Pat. No. 3.449.939 a portable gas sampling and metering-in-air device. Gas meter;ng is effected in the conventional manner by measurement of the voltage across one diagonal of a resistive bridge consisting of e detecting filament and a compensating filament mounted in parallel connection with two resistors, one of which is advantageously adjustable, and the bridge being supplied with electric power along another diagonal.

The Applicant has also proposed in a more general scope in its U.S. Pat. No. 3.587.318 a method and apparatus for measurement of a characteristic quantity of a gaseous medium according to which the value of the quantity considered is appreciated from the measurement of one of the supply power data of a detecting filament where the resistance thereof is kept equal to that of a compensating filament.

In use such explosimeters turn out to give very good results for the explosive gas which was used for the rating thereof whereas with other gases the estimated concentration rates largely deviate from the actual ones.

Such deviations partly result from the differences between the gases, in particular as regards their oxidization heat, combustion temperature, thermal conductivity and above all their diffusion coefficient in air (for example, hydrogen diffuses four times quicker than methane). Such differences influence the renewal of explosive gas at the filament, the quality of combustion (incomplete or premature depending on the filament temperature), the number of calories thus available and their discharge into the surrounding gaseous medium. It is to be noted that such deviations often correspond to underestimation of the actual values, and that this is detrimental to security.

SUMMARY OF THE INVENTION

The object of the invention is to reduce such deviations and to create an improved method of determination of the explosivity rate in a gaseous medium, as well as a device for carrying it out, which are such as to permit to elude at least partly the adverse influence of the mentioned sources of deviations.

To this end, the invention proposes a method for determining the explosivity rate of a gaseous medium containing at least one explosive gas, with a detecting filament which is heated in said medium by an electric current flowing therethrough, comprising the steps of:

igniting said detecting filament through connection thereof to a power supply, regulating power supplied by said power supply to said detecting filament so as to maintain constant the resistance thereof, taking into account, at some successive moments counted from the filament ignition time, the value U(t) of a quantity U which is significant for the power supplied to said detecting filament, extrapolating from said values U(t) an exponential curve of equation $$U(t) = \sum_{i=1}^{i=n} U_{o,i} \exp(-k_i t)$$

by identifying the parameters $U_{o,i}$ and $k_i$ thereof, n being an integer greater or equal to unit, and introducing parameters $U_{o,i}$ and $k_i$ into a process function F adapted to provide from these parameters an estimation of the initial explosivity rate of such gaseous medium independently of the nature of the explosive gas present in such gaseous medium.

The method of this invention is based on the Applicant's discovery that it is surprisingly possible to determine a simple empirical function permitting to relate the mentioned parameters, $U_{o,i}$, pre-exponential coefficients, and $k_2$, exponents, to the explosivity rate $x_o$ of a gaseous mixture, such function being substantially independent of the nature of the gas(es) in presence. The accuracy of the result obviously depends on the precision of the determination of said empirical function as well as on number n of exponential functions which are taken into account; it is however to be kept in mind that obtaining too great accuracy would be illusory since the lower limit of explosivity is an inaccurate concept in itself, because its measurement mainly depends on the method and experimental materials used and on parameters such as temperature. In the general case, in practice, one will choose n=1, or n=2 for a mixture of very different gases.

In case of mixtures of explosive gases the use of this invention requires preselection of a hypothesis on the relationship between the explosivity rate of the mixture and those of the explosive gases taken individually. As a first approximation, there is generally admitted according to LE CHATELIER's law that it is sufficient to sum up the rates of the individual gases. Other hypotheses can however be proposed if need be without departing from the scope of the invention.

According to this invention, due to the utilization of a judiciously chosen funtion F, the explosivity rate of a gaseous medium containing one or more explosive gases is estimated with accuracy substantially independently of the nature of the explosive gas(es) present. Consequently, the method according to the invention, and therefore the devices for carrying it out, are of a universal nature, since they are adaptable without modification to the estimation of the explosivity rate of a large variety of gaseous mediums.

Moreover, it is to be noted that according to the invention, the time elapsed is taken into account and that there is given access to the initial explosivity rate $x_o$ of the gaseous medium, i.e. prior to any disturbance related to the measurement steps.

In a preferred form of embodiment of the invention, there is also used a compensating filament identical to the detecting filament, supplied under analogous conditions in a gaseous medium similar to that of the detecting filament except that it contains no explosive gas, and the quantity U significant for the power supplied to the detecting filament is the difference between the supply voltages to detecting and compensating filaments. Thus, there are eliminated any environment fluctuations that may affect the measurement operations and the results thereof.

More particularly, according to the invention it is appropriate to use as the processing function F, when $n=1$, the ratio, save for a multiplying coefficient, of the pre-exponential parameter $U_o$ of the exponential extrapolated equation, to the exponent k of the latter, or, when n is greater than unit, save for a multiplying coefficient, the sum $$\sum_{i=I}^{i=n} (U_{o,i}/k_i).$$

Such a very simple function does not require more than the use of elementary computing means. Other simple functions are proposed according to the invention; they differ from the above-mentioned one by replacement of denominators by a polynomial functions of $k_i$ in the first degree, the second degree or even the third degree depending on the desired accuracy, on the number and on the nature of the gases that are to be metered by the apparatus.

For the sake of simplicity, it is also contemplated according to the invention to determine the parameters of the exponential extrapolated equation by using an approximative expression of the latter, i.e. its limited development of the first order when $n=1$, or its limited development of the third order when $n=2$.

In view of the dissimilar behaviours of explosive gases, in particular hydrogen as compared to other hydrocarbons, it is also contemplated according to the invention when $n=1$, to introduce parameters $U_o$ and k into a function selected depending on the position of the exponent k as referred to a critical value $k_o$. The Applicant has actually found, in the case of hydrogen which behaves differently from the other hydrocarbons, that there is also a difference between the exponential exponents corresponding to said gas and those of the other hydrocarbons which prove to remain within a narrow range. As an alternative, two pairs of parameters ($U_{o,i}$, $k_i$) are used, one for rapid gases, such as hydrogen, and the other pair for slower gases.

For carrying out the above-mentioned methods there is contemplated according to the invention a device for determining the explosivity rate of a gaseous medium comprising:

a detecting filament disposed in a measurement cell containing the gaseous medium, a regulation circuit comprising a power supply, adapted to electrically feed said detecting filament so as to maintain constant the resistance thereof, an analog-digital converter controlled by counter and time delay means, and a digital processing unit for processing signals supplied by said converter and for determining an estimation of the explosivity rate of the gaseous medium.

In view of the universal nature of the method which is carried out by such device, and of the simple elements composing it, such devices permit to standardize manufacturing series with little unitary costs, resulting into broad spreading of such devices. Therefore, the invention ensures substantial increased security in all sites where explosive gases do exist or might occur.

BRIEF DESCRIPTION OF THE DRAWINGS

Other objects, characteristics and advantages of this invention will appear from the following description which is given by way of example with reference to the attached drawing in which.

DESCRIPTION OF THE PREFERRED EMBODIMENTS

Figure 1:
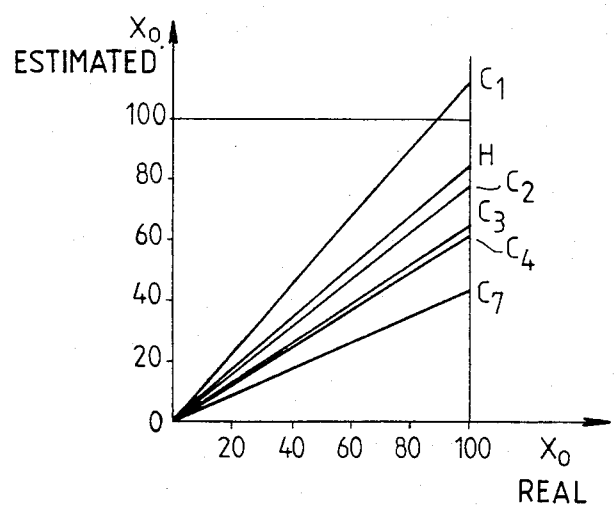
FIG. 1 is a graph showing for different hydrocarbons the explosivity rates estimated by a known explosimeter as a function of the actual rates.

FIG. 1 illustrates differences between the actual and measured explosivity rates, for hydrogen and various hydrocarbons, in association with an explosimeter of a known type, the reference of which is MSA DGE 2000. It is to be noted that such differences correspond practically always to underestimations of the actual rates, which is detrimental to security.

In this graph as well as the following ones, the explosive gases are designated by symbols, the meanings of which are specified in the following table:

$H$ = hydrogen
$C_1$ = methane
$C_2$ = ethylene-ethane
$C_3$ = propane
$C_4$ = butane
$C_5$ = pentane
$C_7$ = heptane-acetone
$C_8$ = octane
$C_{10}$ = decane.

Examination of the graph of FIG. 1 reveals that the measured explosivity rates for a given hydrocarbon are the more underestimated the more such hydrocarbon admits cumbersome molecules, i.e. (as first approximation) those which slowly diffuse in air towards the filament (and viceversa). Such deviations appear therefore to be attributable for a major part to the differences in the diffusion coefficients in air existing between such gases. Hydrogen which is not a hydrocarbon lies notwithstanding its little molecular mass between methane and ethylene.

It may be noted that for a given real explosivity rate $x_o$ there is a difference of about 70% between the results obtained for the extreme gases, methane and heptane. This explains why up to now as many explosimeters have been used as there are explosive gases to be metered.

Figure 2:
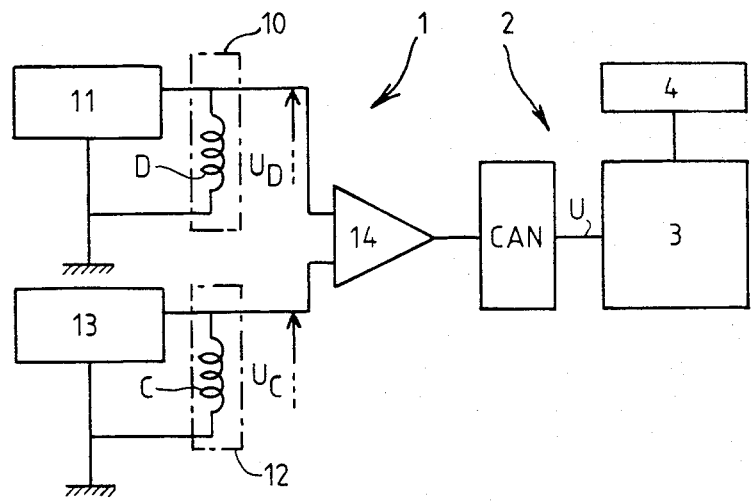
FIG. 2 is a block diagram of a device according to the invention.

According to the invention, one remedies this drawback at least partly by means of a device having a general structure as shown in FIG. 2. The device is composed of an analog measurement portion 1 followed by an analog-digital converter CAN and then digital processing unit 2.

The measurement unit 1 comprises a detecting filament D disposed in a measurement cell 10 containing part of the gaseous medium to be metered. Across the terminals thereof, one of which being grounded, there is disposed a regulation device 11 designed for regulating power supplied to the filament D so as to maintain constant the resistance thereof notwithstanding the oxidization reactions caused thereby, possibly, in the gaseous medium enclosed in the cell 10.

Advantageously, the measurement unit 1 also comprises a compensating filament C identical to the detecting filament and which is placed in a gaseous surrounding analogous to the gaseous medium considered, but free of any explosive gas, enclosed in a second measurement cell 12. The compensating filament is included in a circuit means analogous to that of the detecting filament, with a regulator 13, analogous to regulator 11, modulating the power supply so as to maintain constant the resistance of said compensating filament.

The terminals of those filaments, when not grounded, are connected to the inputs to a comparator 14, for example adapted to measure the voltage difference between such terminals. This comparison of the power supplied to both of the filaments permits to cancel the influence of fluctuant experimental parameters, mainly variations of external temperature and wear of the detecting filament. Regarding this point it is specified that the detecting and compensating filaments are advantageously replaced simultaneously.

The output from the comparator 14 is connected to the input to the analog-digital converter CAN, followed by a computing element 3 completed by a display element 4.

Figure 3:
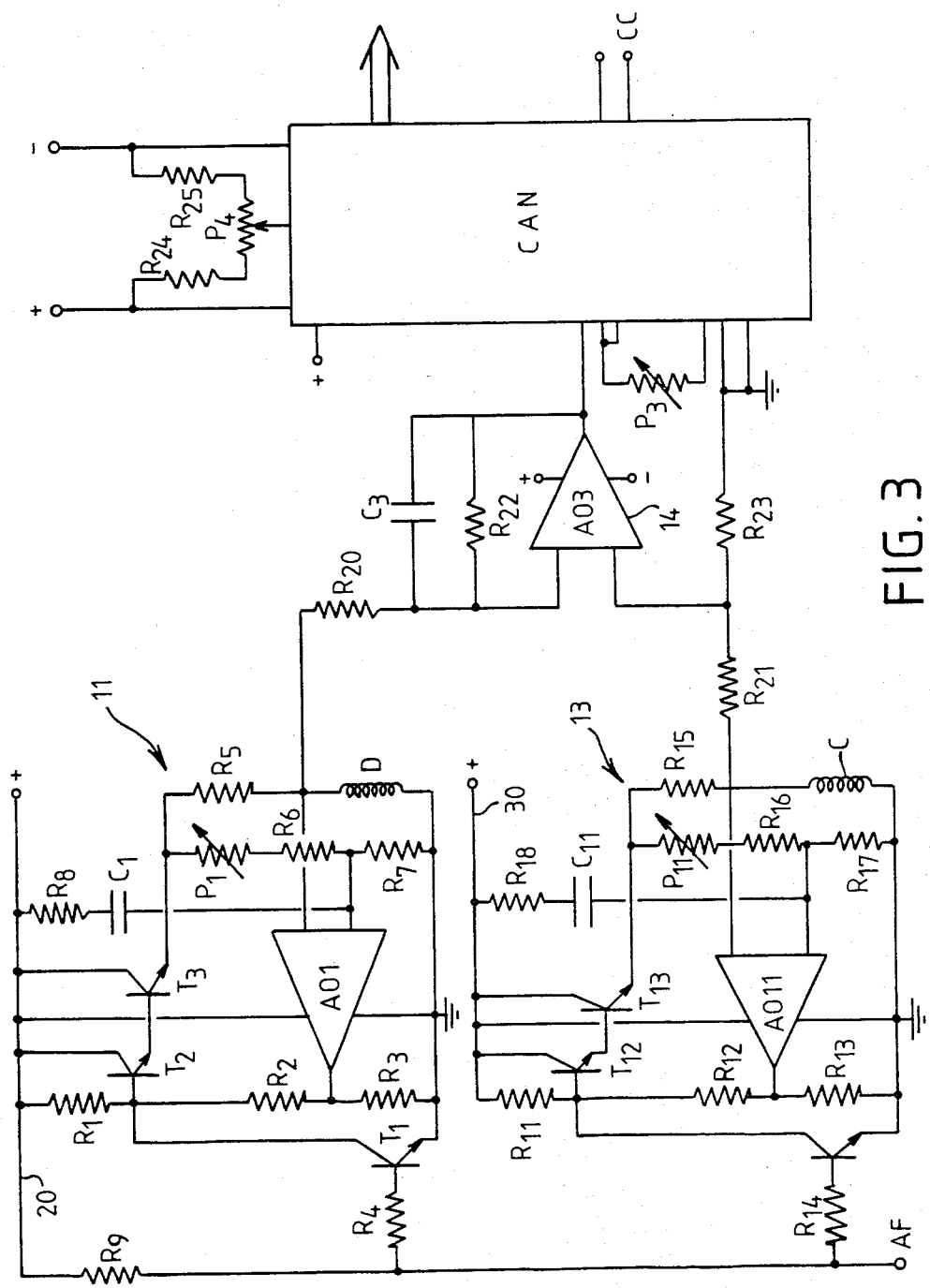
FIG. 3 is a detailed view of the analog section of such a device.

The structure of the analog measurement section 1 is shown in detail in FIG. 3. Regulators 11 and 13 have the same structure. The following description is limited to regulator 11. The elements in regulator 13 are designated by reference numerals obtained by adding 10 to those of the corresponding elements in regulator 11.

The regulator 11 of the detecting filament D comprises a supply power bus 20 of constant potential (5 V in the proposed example). A resistive line formed of resistors $R_1$, $R_2$, $R_3$ mounted in series connection is disposed between said bus 20 and ground. Resistors $R_2$ and $R_3$ are mounted between collector and emitter of a transistor $T_1$ forming the ignition element, the base of which is connected across a resistor $R_4$ to a filament ignition terminal AF. The common terminal of resistors $R_1$ and $R_2$ is to the base of a transistor $T_2$, the emitter of which is in its turn to the base of a second transistor $T_3$. The collectors of transistors $T_2$ and $T_3$ are connected to bus 20, whereas the emitter of $T_3$ is connected to the ground through a resistive bridge in which filament D is included. Such bridge comprises a resistor $R_5$ and D, on the one hand, and, on the other hand, a resistor $R_6$ in series connection with a variable resistance $P_1$ and a resistor $R_7$. An operational amplifier A01 the inputs of which are mounted along the transverse diagonal of the resistive bridge has its output connected to the junction of resistors R2 and R3. The junction $R_6$-$R_7$ is advantageously connected to the power supply bus 20 through a circuit ($C_1 + R_8$) for dampening oscillations caused by thermal inertia of the filament.

The terminal AF to which the analogous resistors $R_4$ and $R_{14}$ are connected is connected to bus 20 through a resistor $R_9$.

The terminals of filaments D and C connected to the associated operational amplifiers are connected through resistors $R_{20}$ and $R_{21}$ to the inputs of an operational comparison amplifier A03 the output of which is connected to the analog input of the analog-digital converter CAN. Such output from the comparison element A03 is coupled through $C_3$ and $R_{22}$ in parallel relationship to its input from the detecting filament, whereas the input from the compensating filament is connected to ground through a resistor $R_{23}$.

The converter CAN has conventionally a 12-bit parallel output. Two potentiometers $P_3$ and $P_4$ permit gain adjustment and zero offset respectively.

Figure 4:
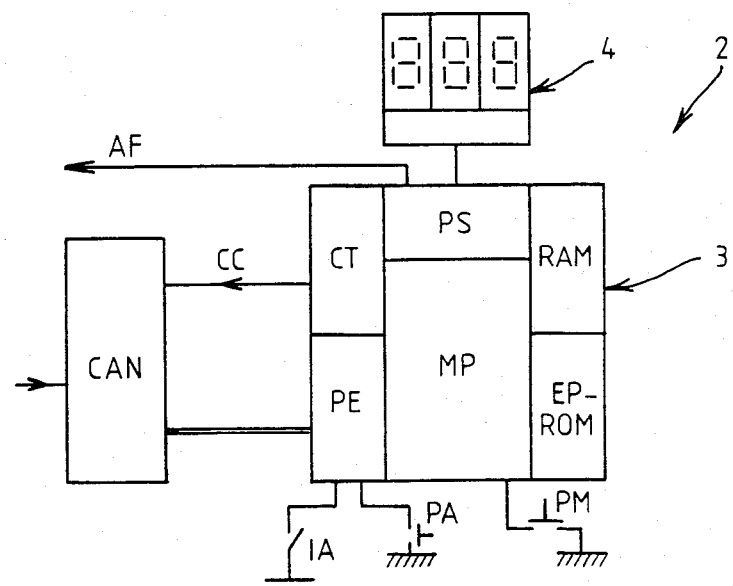
FIG. 4 is a schematic view of the digital section of such a device.

The digital processing unit 2 is shown schematically in FIG. 4. It substantially comprises a micro-processor MP surrounded by its peripheral devices, followed by the display element 4.

Microprocessor MP is connected to converter CAN through an input port PE which also comprises bits for control through an auxiliary switch IA adapted to select, if need be, a digital computing option and through a push-button PA provided for forwarding an interrupt signal to the microprocessor, in addition to those associated to each conversion.

The peripheral devices of the microprocessor MP are substantially a program memory EPROM, a data memory RAM, decoders for selecting circuits and a counter and delay means CT which among other functions is used for example to control every second an analog-digital conversion (signal CC).

The results appear on the output bits from the output port PS. They are taken into account by the decoders (three decoders in the example considered) which control an equal number of seven-segment display means LED. The port PS also comprises bits for the control of the decimal points as well as a filament ignition control (terminal AF).

A measurement push-button PM causes resetting of all the circuits and starts the microprocessor at the beginning of the program.

Interconnections between the various elements are made conventionally, save for terminals $M_1$ of the input and output ports, which are connected to push-button PM.

At rest, the signal applied at AF makes transistors $T_1$ and $T_{11}$ conductive, thereby short circuiting the power supply elements $T_2$, $T_3$, $T_{12}$ and $T_{13}$, and no current feeds the filaments.

Depression of push-button PM causes a signal to appear at AF. The base of transistors $T_1$ and $T_{11}$ are at a low level so that they are non conductive, whereas transistors $T_2$, $T_3$, $T_{12}$ and $T_{13}$ become conductive. For example, in case of the detecting filament, being controlled by comparator A01 as a function of the voltage difference across the input terminals of the latter, transistors $T_1$ and $T_2$ regulate the current in the resistive bridge of D in such a way that the resistance of the detecting filament is equal to $(R_5.R_7)/(P_1+R_6)$, this value being adjustable by acting upon potentiometer $P_1$. The same reasoning applies to the compensating filament. It will be noted that such system accelerates the heating of the filaments since it maintains them at an overvoltage as long as the desired temperature has not been reached.

The voltage across the terminals of the filaments are subtracted from one another through the comparator A03, and their difference is converted at repeated times through the converter CAN which thus ensures at successive times that a significant quantity U of the filament power supply is taken into account.

The digital processing unit 3 takes into account several successive values U(t) of such quantity U, then extrapolates from those values an exponential function, the equation of which is $$U(t) = \sum_{i=I}^{i=n} U_{o,i} \cdot \exp(-k_i \cdot t),$$

with n being a preselected integer greater or equal to 1, of which parameters $U_{o,i}$ and $k_i$ are identified. These are then introduced into an empirically defined process function which produces from such parameters an estimate of the initial explosivity rate $x_o$ of the gaseous mixture considered. In the general case, n=I and only one pair of parameters $(U_o, k)$ is used.

A device of the above-mentioned type and the method carried out thereby make it possible to obviate the requirement of identifying the explosive gas(es) present in the considered medium, in as much as the Applicant has discovered that it was possible to determine empirically such a process function $x_o=F(U_{o,i}k_i)$, which is independent of the nature of the gas(es) present.

The form of such process function can mainly be established on the base of the following theoretical considerations.

Let [G] be a concentration of a gas G diluted in a medium such as air, $\Delta_H$ its oxidization enthalpy, and D its diffusion coefficient in the gaseous medium considered. It results from an article by FIRTH, JONES and JONES (Combustion and Flame, 21 (1973), 303–311) that gas G upon contacting a heated filament gives thereto an energy Q which in permanent operation and at constant temperature can be expressed as follows if catharometric phenomena are neglected:

$$Q=K. \Delta H. D. [G] \qquad (1)$$

where K is a; characteristic constant of the filament.

By passing from energy Q to the calorific power P released by the combustion of gas G, and by introducing the concept of explosivity rate x defined by:

$$x=[G]/[G]_{LIE} \qquad (2)$$

there is obtained, $K_1$ being also a characteristic constant of the filament:

$$P=K_1. H. [G]_{LIE}. D .x \qquad (3)$$

which becomes:

$$P=K_1. K_2. D .x \qquad (4)$$

by laying down $$K_2=\Delta H . [G]_{LIE} \qquad (5)$$

FIRTH, JONES and JONES have moreover observed that coefficient $K_2$, a characteristic quantity for each gas, little varies from one hydrocarbon to another.

Practically, in a measurement cell the gas runs short in the course of time so that the operational conditions are not permanent. In view of the low concentrations of the gases to be measured, the consumption of gas is approximated by means of a first order kinetics. There is deduced therefrom :

$$x=x_o. \exp(-kt) \qquad (6)$$

$x_o$ being the explosivity rate at the time t=0.

By comparing the expression for the calorific energy supplied by the gas during combustion thereof as obtained by integrating equation (4)in t between 0 and infinite, and its thermo-chemical expression, it can be derived that k is proportional to the diffusion coefficient D.

It is verified that U is an experimental quantity representative of power P, which admits the following approximated expression:

$$U=U_o. \exp(-k.t) \qquad (6')$$

with, $K_3$ being a characteristic constant of the device:

$$U_o=K_3. K_2. D .x_o \qquad (7)$$

It is deduced therefrom that the ratio $U_o/k$ does not explicitly depend on D, hence the expression for $x_o$ independent of coefficient D :

$$x_o = F(U_o, k) = K_4 \cdot K_2 \frac{U_o}{k} \qquad (8)$$

$K_4$ being a constant.

In as much as it is admitted on the basis of the above-mentioned observations of FIRTH et al. that $K_2$ does not depend on the nature of the gases, it results that function F defined by equation (8) constitutes a process function within the above specified meaning.

In the case of a mixture of gases $G_1$ and $G_2$, LE CHATELIER's law teaches that the total explosivity rate x may be expressed as the sum of individual explosivity rates:

$$x=x_1+x_2$$

$$x=x_{0,1}.\exp(-k_1.t)+x_{0,2}.\exp(-k_2.t) \qquad (6bis)$$

and $$x_0=x_{0,1}+x_{0,2}$$

By laying down:

$$U = U_{0,1}.\exp(-k_1.t) + U_{0,2}.\exp(-k_2.t) \qquad (6'bis)$$

there results by approximation:

$$x_0 = F_1(U_{0,1}, k_1, U_{0,2}, k_2)$$

$$x_0 = A.(U_{0,1}/k_1 + U_{0,2}/k_2) \qquad (8bis)$$

In view of the fact that equation (1) is only valid at a constant temperature, the process equation deduced from equation (8) requires that the resistance of the filaments be kept to a constant value, hence providing regulators 11 and 13 in a device according to the invention.

For the sake of simplicity, it is contemplated according to the invention to determine the pre-exponential $U_o$ and exponent k parameters from the first order term of the limited development of the exponential equation:

$$U(t) = U_o \cdot (1 - k.t) \qquad (9)$$

The determination of parameters $U_o$ and k, associated to one gas, or to a gaseous mixture considered as a single gas, only requires that the processing unit 3 should take into account data corresponding to two times or moments. These advantageously correspond to measurement durations which correspond to simple ratios, for example from the simple to the double, thereby significantly simplifying computation. The utilization of data corresponding to more than two times may be preferred for improving accuracy on $U_o$ and k on the condition that the corresponding times are compatible with the simplifying hypotheses used.

This invention actually specifies to take into account the values of the significant power supply quantities selected at three times corresponding to time intervals that satisfy to simple ratios (for example: 1s, 2s and 4s); there is treated successively at least two of the so obtained couples of values (for example: 1s and 2s; 2s and 4s); and the values $U_o$ and k deduced therefrom are compared to one another. Comparison of such values gives an estimate of the reliability of the final estimates of the explosivity rate $x_o$, or even is used as a basis for obtaining corrected values, in case of a gaseous mixture.

Figure 5:
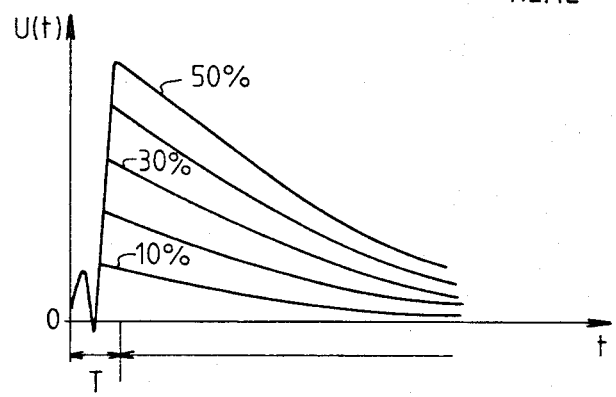
FIG. 5 is a graph showing the development in time of quantity U.

FIG. 5 shows the development of signal U as a function of the time elapsed since ignition of the filaments, for a given hydrocarbon, for various explosivity rates. It may be noted that the curves can be described beyond about 1s by a law of the exponential type thereby justifying the relation (6). A transient rate of filament heating and of stabilization (between about 0.5 and 1s), denoted as T, appears at the beginning of such curves thereby making any measurement impossible.

Figure 6:
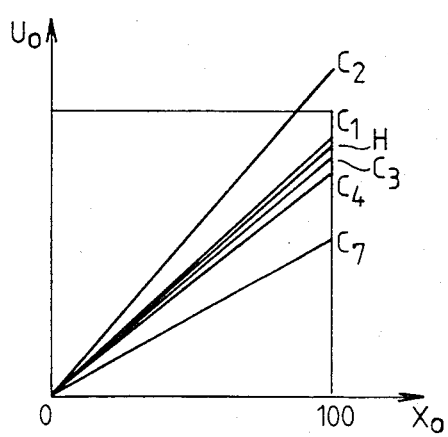
FIG. 6 is a graph showing for different hydrocarbons and hydrogen the correlation between the parameter $U_o$ and the actual explosivity rate in air.
Figure 7:
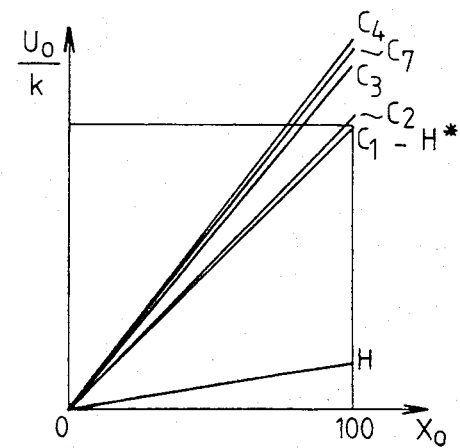
FIG. 7 is a graph showing for various hydrocarbons and hydrogen the correlation between the ratio $U_o/k$ and the actual explosivity rate in air.

FIGS. 6 and 7 correlate explosivity rates estimated by a device in accordance with the invention for two simple process functions (after taking into account U after 2s and 4s) with the actual rates.

FIG. 6 corresponds to an extremely simplified process function since it leads to estimation of the explosivity rates from the single parameter $U_o$; however this function has the advantage as compared to the prior art to take into account the time elapsed during the measurement steps. The deviations between the extreme curves are however of the same order of magnitude than those of FIG. 1.

On the other hand, utilization of relation (8) as the process function leads to much aore substantial results since FIG. 7 only shows maximum deviation of about 30%, i.e. practically a decrease by half as compared to FIG. 6.

It is to be noted that in FIG. 7 the curves can no longer be classified as in FIG. 1, as a function of molecular sizes.

FIG. 7 comprises two curves associated to hydrogen. The curve corresponding to H* results from supplementary correction required by the particular characteristics of hydrogen with respect to hydrocarbons. As a matter of fact, hydrogen has a coefficient $K_2$ five times smaller than hydrocarbons, but has higher coefficient D (four times that of methane). Its presence can however be easily detected according to the invention in as much as hydrogen presents k values differing much from those of hydrocarbons. It is sufficient to include into the digital data processing a comparison step for comparing exponent k of the exponential to a value $k_o$ selected between the range of values associated to hydrogen and that associated to hydrocarbons. If k is lower than $k_o$, then the operations associated to relation (8) are carried out, otherwise a multiplication coefficient specific to hydrogen is to intervene.

Figure 8:
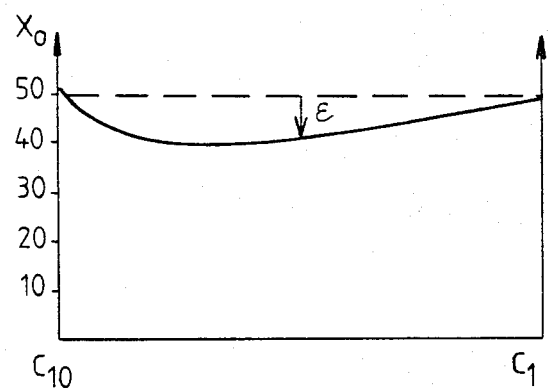
FIG. 8 is a diagram showing the explosivity rate of a mixture of methane and decane estimated according to a method of the invention as a function of the methane concentration.
Figure 9:
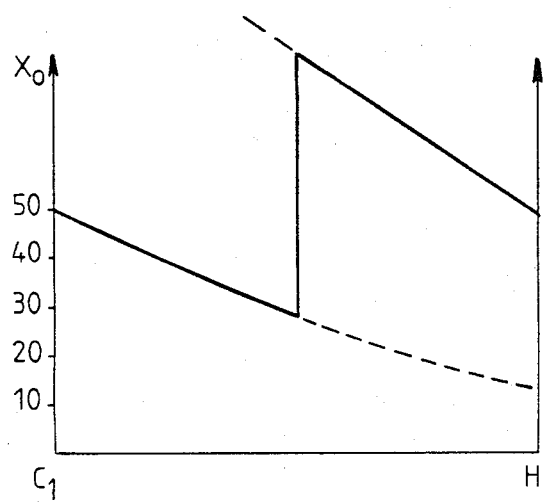
FIG. 9 is a diagram similar to the preceding one corresponding to a mixture of hydrogen and methane.

FIGS. 8 and 9 correspond to the metering, not of a single gas, but rather of a mixture of two gases. The curves represented therein result from the application of the digital processing which was just defined above to the experimental values contained in the above-mentioned article by FIRTH et al.

In case of two hydrocarbons, most different as to diffusion (methane and decane), it is observed that the process function of equation (8) leads to an underestimation of the rate of maximum about 20%, which is fully satisfactory. Relation (8) therefore appears to be particularly well adapted to the metering of hydrocarbons, whether alone or in admixture.

When hydrogen participates in the gaseous medium the same does not apply as appears from FIG. 9. The introduction of the above-mentioned correction specific to hydrogen leads to a vertical segment extending from an underestimation of the actual rate of about 40% to an overestimation of 60%.

The horizontal position of such segment depends on the selected critical value $k_o$. The bottom curves corresponds to the application of the relation (8) which leads for hydrogen to a clear underestimation of its explosivity rate (see FIG. 7, curve H). The upper curve corresponds to multiplication of the values of the bottom curve by the multiplying coefficient specific to hydrogen.

Figure 10:
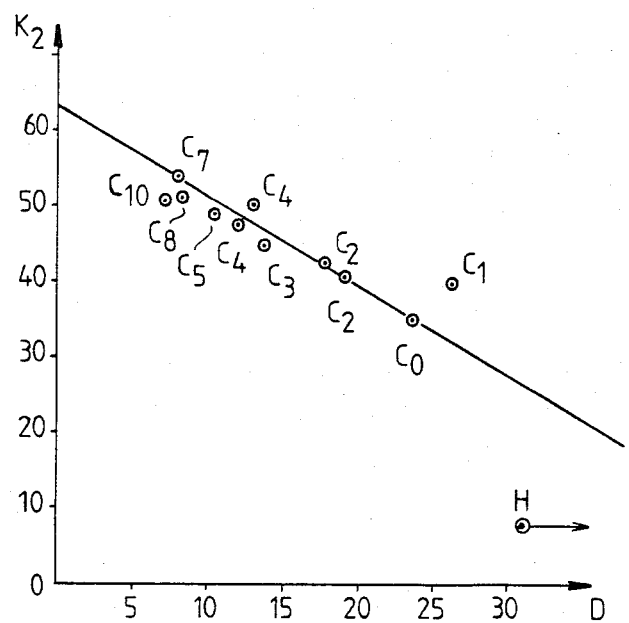
FIG. 10 is a graph showing for various explosive gases the correlation between a characteristic quantity $K_2$ and the diffusion coefficient in air D.

Such disparities in the results actually originate from the fact that coefficient $K_2$ varies from one hydrocarbon to the other, from one explosive gas to the other (H, CO ... ), as appears from examination of FIG. 10.

To take such variations into account it is specified according to the invention to modify correspondingly, when this appears to be useful, the form of the process function used for processing $U_o$ and k.

Figure 11:
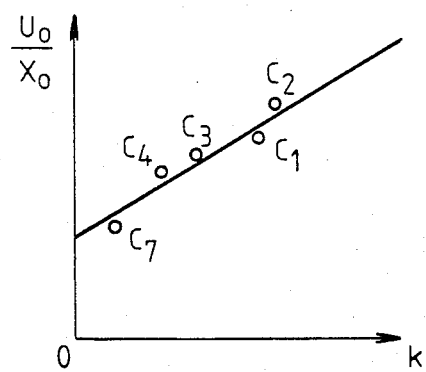
FIG. 11 is a graph showing for various hydrocarbons the correlation between the ratio $U_o/x_o$ and parameter k.

Thus, in accordance with this invention, there is proposed a first amended form of the process function:

$$x_o = F(U_o, k) = B \cdot \frac{U_o}{k + b} \qquad (10)$$

the justification of which appears in FIG. 11, showing the ratio of the second parameter $U_o$ to the actual explosivity rate $x_o$ for several hydrocarbons, as a function of the measured value of parameter k. A straight line substantially passing through these points can be drawn but it does not pass through the origin as implied by relation (8), hence the intervention of a coefficient b in relation (10).

Another process function may be deduced from the mentioned FIG. 10 from the straight line drawn therein, which passes very close to the points appearing therein. By carrying over the expression for $K_2$ as a function of D, which may be deduced therefrom, into equation (7) and eliminating D between this equation and the expression for k, a new process function F''' analogous to F' can be defined, but its denominator is a k polynomial of the second degree.

Figure 12:
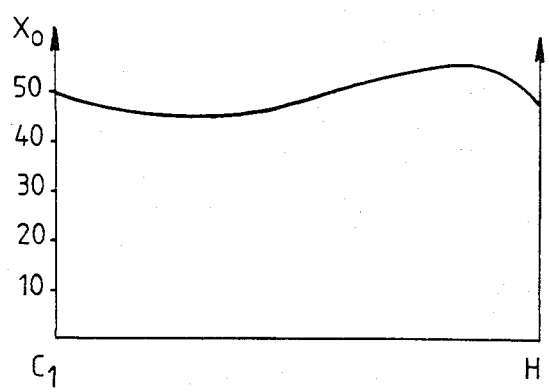
FIG. 12 is a diagram similar to that of FIG. 9 showing an estimate according to an improved method of the invention.

If other points such as hydrogen or other explosive gases differing from hydrocarbons are brought into FIG. 11, then the whole of the points drawn in this manner can suitably be described by a polynomial curve of the third degree. By bringing such polynomial into the denominator of the process function, the Applicant has shown that this new process function leads to a good approximation of the explosivity rate of a mixture containing hydrogen as shown by FIG. 12, which corresponds to the methane and hydrogen mixture of FIG. 9.

As an alternative, the gaseous mixture under consideration is assimilated to a mixture of two (or more) more or less imaginary gases, and corresponding parameters $U_{0,1}$, $k_1$, $U_{0,2}$, $k_2$ in equation (6'bis) are identified; one calculates the explosivity rates of these imaginary gases and one adds them up according to equation (8 bis), or to more elaborated equation. This alternative has the advantage that quick and slow gases may be processed separately. In practice a limited development of the third order of the exponential functions will be sufficient for identifying parameters $U_{o,i}$ and $k_i$ since it will provide four coefficients from which the four parameters under consideration may be deduced: it requires at least four experimental values of U(t).

As an alternative, when values of U are taken into account at successive times which all are multiples of a time $t_1$, said values can be expressed as functions of $U_{0,1}$ and $U_{0,2}$, and also of exp ($-k_1.t_1$) and exp ($-k_2.t_1$). These parameters can be deduced from at least four values of U(t); $k_1$ and $k_2$ are then identified in an exponential form and are preferably introduced, in such form, in an appropriate process function.

Therefore, it appears that many process functions can be proposed within the scope of this invention. Such functions defined empirically are obviously of an increasingly complex shape as a greater accuracy is desired, as many gases are in presence and as the number of gases capable of being metered alone or in admixture with others is high. In practice, such a process function is established from experimental pairs of calibration parameters ($U_o{}^c/x_o{}^c,k^c$) obtained for a selection of reference gases or gaseous mixtures. The form of an empirical function f is arbitrarily chosen, by which a correlation between these pairs of calibration parameters ($U_o{}^c/x_o{}^c,k^c$) is to be expressed, and coefficients of this function f is chosen in form of a polynomial in k, of low degree preferably. In operation of the device the explosivity rate $x_o$ is then given by the ratio $U_o/f(k)$ in the case of one imaginary gas to be metered, or by ($U_{0,1}/f(k_1)+U_{0,2}/f(k_2)$) in the case of a mixture of two gases to be metered.

In case of the process function defined by equation (8), it is specified according to the invention to calibrate the metering device with methane since as appears from FIG. 7 all the measurements will be overestimated in case of practically, or almost pure gases, so that security will be improved.

It will be understood that many modified forms of embodiment may be proposed by the man of the art without however departing from the scope of the invention both as regards the filament (nature), the measurement cell (form, volume), the regulating device, the comparator, the converter, and the digital processing unit, and its display elements. In the same manner, the experimental parameters may be selected within a broad range of values (filament temperature or resistance).

Although the invention was described in case of a gaseous medium based on air it can obviously apply to any other gaseous surrounding, of which the explosivity rate must remain limited.

Thus, the invention has a very extensive field of application including mines and chemical industries where it is desired to prevent any leak of explosive gas. A device according to the invention can then be stationary so that, when a critical explosivity rate is exceeded, alarm signals and emergency measures are automatically initiated.

We claim:
1. A method of determining the explosivity rate of a gaseous medium containing at least one explosive gas, with a detecting filament which is heated in said medium by an electric current flowing therethrough, comprising the steps of:
igniting said detecting filament through connection thereof to a power supply,
regulating power supplied by said power supply to said detecting filament so as to maintain constant the resistance thereof,
taking into account, at some successive moments counted from the filament ignition time, the value U(t) of a quantity U which is significant for the power supplied to said detecting filament,
extrapolating from said values U(t) an exponential curve of equation

$$U(t) = \sum_{i=I}^{i=n} U_{o,i} \cdot \exp(-k_i \cdot t)$$

by identifying the parameters $U_{o,i}$ and $k_i$ thereof, n being an integer greater or equal to unit $k_i$ being a positive real exponent expressed in $\sec^{-1}$, and
introducing parameters $U_{o,i}$ and $k_i$ into a process function F, where the process function F is an empirically predetermined mathematical function with twice n parameters, which process function F is adapted to provide from these parameters an estimation of the initial explosivity rate of such gaseous medium independently of the nature of the explosive gas present in such gaseous medium.

2. A method according to claim 1, further comprising the steps of:
igniting, at the same time that said detecting filament is ignited, a compensating filament, identical to said detecting filament, located in a gaseous medium analogous to that of the latter except that it contains no explosive gas, through connection thereof to a power supply,
regulating power supplied to said compensating filament so as to maintain constant the resistance thereof, and obtaining the quantity U by subtracting supply voltage of said compensating filament from supply voltage of said detecting filament.

3. A method according to claim 2, whereby said estimation of the initial explosivity rate is obtained, when n=1, by dividing $U_o$ by a polynomial in k or, when n is greater than unit, by adding up parameters $U_{o,i}$, each one being divided by the same polynomial in $k_i$.

4. A method according to claim 3, whereby said estimation of the initial explosivity rate is obtained, save for a multiplying constant, by dividing $U_o$ by k when n=1, or by adding up the ratios $U_{o,i}/k_i$ when n is greater than unit.

5. A method according to claim 2, whereby said exponential curve is extrapolated in the form $U(t)=U_o.\exp(-k.t)$, n being equal to unit.

6. A method according to claim 5, whereby parameters $U_o$ and k are obtained from the values $U(t)$ by approximating the exponential function by its limited development of the first order.

7. A method according to claim 6, whereby the times relative to two successive values of $U(t)$, counted from the ignition of the detecting filament, satisfy a ratio of 1 to 2.

8. A method according to claim 7, whereby values $U(t)$ are taken into account at three successive instants.

9. A method according to claim 5, whereby parameters $U_o$ and k are introduced in one function which is selected from a plurality of two functions depending on the value of k as compared to a critical value $k_o$.

10. A method, according to claim 1, whereby
said detecting filament is located in a measurement cell containing said gaseous medium to be metered,
a regulation circuit comprising a power supply is provided for electrically feeding said detecting filament in such a manner that resistance of said detecting filament is maintained constant,
an analog-digital converter controlled by counter and time delay means is provided for converting in digital signals at some successive moments the value of said quantity significant for power supplied to said detecting filament, and
a digital processing unit is provided for processing said digital signals through said process function F and for determining said estimation of the explosivity rate of gaseous medium to be metered.

11. A method according to claim 10, whereby it is further provided
a compensating filament, identical to said detecting filament, located in a measurement cell which is near said measurement cell of said detecting filament but which does not contain any explosive gas,
a regulation circuit for electrically feeding said compensating filament in such a manner that resistance thereof is maintained constant, and
a comparison circuit for providing difference between voltages supplied to said detecting and compensating filaments to said analog-digital converter.

12. A method according to claim 11, whereby each of said regulation circuits comprise a resistive bridge with two pairs of opposed terminals and including one of said filaments, one pair of opposed terminals being electrically fed through a supply circuit, and the other pair of opposed terminals being connected to a comparator member controlling said supply circuits.

13. A method according to claim 12, whereby said regulation circuits further comprise damping means for damping thermal oscillations of said filaments.

14. A method according to claim 11, wherein said regulation circuits are controlled by said digital processing unit through an ignition circuit.

15. A method according to claim 10, wherein said digital processing unit allows for two different calculation options giving an estimation of explosivity rate of gaseous medium to be metered as a function of digital signals produced by said analog-digital converter.

16. A method according to claim 10, wherein said digital processing unit uses processing data stored during calibration of said device with methane.

17. A device for determining the explosivity rate of a gaseous medium comprising:
a detecting filament located in a measurement cell containing gaseous medium to be metered,
a regulation circuit comprising a power supply for electrically feeding said detecting filament in such a manner that resistance of said detecting filament is maintained constant,
an analog-digital converter electrically connected to said detecting filament,
a counter and time delay means controlling said analog-digital converter so as to convert in digital signals at some successive moments the value of a quantity significant for power supplied to said detecting filament, and
a digital processing unit for processing said digital signals and for determining an estimation of the explosivity rate of gaseous medium to be metered.

18. A device according to claim 17, further comprising:
a compensating filament, identical to said detecting filament, located in a measurement cell which is near said measurement cell of said detecting filament but which does not contain any explosive gas,
a regulation circuit for electrically feeding said compensating filament in such a manner that resistance thereof is maintained constant, and
a comparison circuit for providing difference between voltages supplied to said detecting and compensating filaments to said analog-digital converter.

19. A device according to claim 17, wherein each of said regulation circuit comprises a resistive bridge with two pairs of opposed terminals and including one of said filaments, one pair of opposed terminals being electrically fed through a supply circuit, and the other pair of opposed terminals being connected to a comparator member controlling said supply circuit.

20. A device according to claim 19, wherein said regulation circuits further comprise damping means for damping thermal oscillations of said filaments.

21. A device according to claim 17, wherein said regulation circuit is controlled by said digital processing unit through an ignition circuit.

22. A device according to claim 17, wherein said digital processing unit allows for two different calculation options giving an estimation of explosivity rate of gaseous medium to be metered as a function of digital signals produced by said analog-digital converter.

23. A device according to any of claim 17, wherein said digital processing unit uses processing data stored during calibration of said device with methane.

* * * * *